(12) United States Patent
Walker et al.

(10) Patent No.: US 8,591,467 B2
(45) Date of Patent: Nov. 26, 2013

(54) VASCULAR ACCESS ASSEMBLY AND SAFETY DEVICE

(75) Inventors: Sandra Walker, St. Charles, MO (US); Gregory A. Steube, St. Charles, MO (US); Kevin R. Martz, Desoto, MO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/556,451

(22) Filed: Jul. 24, 2012

(65) Prior Publication Data

US 2013/0030370 A1 Jan. 31, 2013

Related U.S. Application Data

(60) Provisional application No. 61/511,187, filed on Jul. 25, 2011.

(51) Int. Cl.
*A61M 5/178* (2006.01)
*A61M 5/00* (2006.01)

(52) U.S. Cl.
USPC ............... 604/164.08; 604/110; 604/164.01

(58) Field of Classification Search
USPC .................. 604/164.08, 110, 263, 164.01
See application file for complete search history.

(56) References Cited

U.S. PATENT DOCUMENTS

| | | |
|---|---|---|
| 4,944,725 A | 7/1990 | McDonald |
| 5,135,504 A | 8/1992 | McLees |
| 5,215,528 A | 6/1993 | Purdy et al. |
| 5,256,152 A | 10/1993 | Marks |
| 5,295,963 A | 3/1994 | Deeks |
| 5,304,136 A | 4/1994 | Erskine et al. |
| 5,385,550 A | 1/1995 | Su et al. |
| 5,395,346 A | 3/1995 | Maggioni |
| 5,405,323 A | 4/1995 | Rogers et al. |
| 5,411,492 A | 5/1995 | Sturman et al. |
| 5,423,766 A | 6/1995 | Di Cesare |
| 5,447,501 A | 9/1995 | Karlsson et al. |
| 5,456,675 A | 10/1995 | Wolbring et al. |
| 5,458,658 A | 10/1995 | Sircom |
| 5,538,508 A | 7/1996 | Steyn |
| 5,554,131 A | 9/1996 | Lacivita |
| 5,558,651 A | 9/1996 | Crawford et al. |
| 5,569,209 A | 10/1996 | Roitman |
| 5,584,809 A | 12/1996 | Gaba |
| 5,584,810 A | 12/1996 | Brimhall |
| 5,599,310 A | 2/1997 | Bogert |
| 5,601,532 A | 2/1997 | Gaba |

(Continued)

FOREIGN PATENT DOCUMENTS

| WO | WO 92/18182 | 10/1992 |
|---|---|---|
| WO | WO 2009/142878 | 11/2009 |

OTHER PUBLICATIONS

International Search Report dated Nov. 2, 2012 in copending PCT/US2012/04839.

*Primary Examiner* — Nicholas Lucchesi
*Assistant Examiner* — Benjamin Koo
(74) *Attorney, Agent, or Firm* — Lisa E. Winsor, Esq.

(57) ABSTRACT

A plurality of different vascular access assemblies are described which protect a clinician from accidental needle stick injury upon withdrawal of a needle from a catheter assembly. Each of the vascular access assemblies include a safety device for guarding the needle tip of the needle upon withdrawal of a needle from the catheter assembly.

8 Claims, 18 Drawing Sheets

(56) References Cited

U.S. PATENT DOCUMENTS

| | | | |
|---|---|---|---|
| 5,651,772 | A | 7/1997 | Arnett |
| 5,672,161 | A | 9/1997 | Allen et al. |
| 5,683,365 | A | 11/1997 | Brown et al. |
| 5,697,907 | A | 12/1997 | Gaba |
| 5,735,827 | A | 4/1998 | Adwers et al. |
| 5,743,891 | A | 4/1998 | Tolkoff et al. |
| 5,746,718 | A | 5/1998 | Steyn |
| 5,755,699 | A | 5/1998 | Blecher et al. |
| 5,800,403 | A | 9/1998 | Pressly, Sr. et al. |
| 5,865,806 | A | 2/1999 | Howell |
| 5,879,331 | A | 3/1999 | Osterlind |
| 5,879,337 | A | 3/1999 | Kuracina et al. |
| 5,911,705 | A | 6/1999 | Howell |
| 5,911,710 | A | 6/1999 | Barry et al. |
| 5,951,515 | A | 9/1999 | Osterlind |
| 5,957,887 | A | 9/1999 | Osterlind et al. |
| 5,967,490 | A | 10/1999 | Pike |
| 5,997,507 | A | 12/1999 | Dysarz |
| 6,001,080 | A | 12/1999 | Kuracina et al. |
| 6,004,294 | A | 12/1999 | Brimhall et al. |
| 6,012,213 | A | 1/2000 | Chang et al. |
| 6,117,108 | A * | 9/2000 | Woehr et al. .................. 604/110 |
| 6,224,569 | B1 | 5/2001 | Brimhall |
| 6,443,929 | B1 | 9/2002 | Kuracina |
| 6,592,556 | B1 | 7/2003 | Thorne |
| 6,595,954 | B1 | 7/2003 | Luther |
| 6,595,955 | B2 * | 7/2003 | Ferguson et al. ............. 604/110 |
| 6,616,630 | B1 | 9/2003 | Woehr |
| 6,652,490 | B2 | 11/2003 | Howell |
| 6,699,221 | B2 | 3/2004 | Vaillancourt |
| 6,709,419 | B2 | 3/2004 | Woehr |
| 6,749,588 | B1 | 6/2004 | Howell |
| 6,761,706 | B2 | 7/2004 | Vaillancourt |
| 6,916,311 | B2 | 7/2005 | Vojtasek |
| 6,981,965 | B2 | 1/2006 | Luther |
| 7,008,404 | B2 | 3/2006 | Nakajima |
| 7,037,292 | B2 | 5/2006 | Carlyon |
| 7,214,208 | B2 | 5/2007 | Vaillancourt |
| 7,214,211 | B2 | 5/2007 | Woehr |
| 7,238,169 | B2 | 7/2007 | Takagi |
| 7,247,148 | B2 | 7/2007 | Murashita |
| 7,264,613 | B2 | 9/2007 | Woehr |
| 7,374,554 | B2 | 5/2008 | Menzi |
| 7,500,965 | B2 | 3/2009 | Menzi |
| 7,513,887 | B2 | 4/2009 | Halseth |
| 7,513,888 | B2 | 4/2009 | Sircom |
| 7,530,965 | B2 | 5/2009 | Villa |
| 7,534,227 | B2 | 5/2009 | Kulli |
| 7,597,681 | B2 | 10/2009 | Sutton |
| 7,611,487 | B2 | 11/2009 | Woehr |
| 7,611,499 | B2 | 11/2009 | Woehr |
| 7,654,988 | B2 | 2/2010 | Moulton |
| 7,682,331 | B2 | 3/2010 | Carrez |
| 7,722,569 | B2 | 5/2010 | Soderholm |
| 7,736,339 | B2 | 6/2010 | Woehr |
| 7,744,567 | B2 | 6/2010 | Glowacki |
| 7,736,332 | B2 | 7/2010 | Carlyon |
| 7,828,773 | B2 | 11/2010 | Swisher |
| 7,828,774 | B2 | 11/2010 | Harding |
| 7,850,650 | B2 | 12/2010 | Breitweiser |
| 7,905,857 | B2 | 3/2011 | Swisher |
| 2007/0191774 | A1 | 8/2007 | Carrez |
| 2009/0292243 | A1 | 11/2009 | Harding et al. |

* cited by examiner

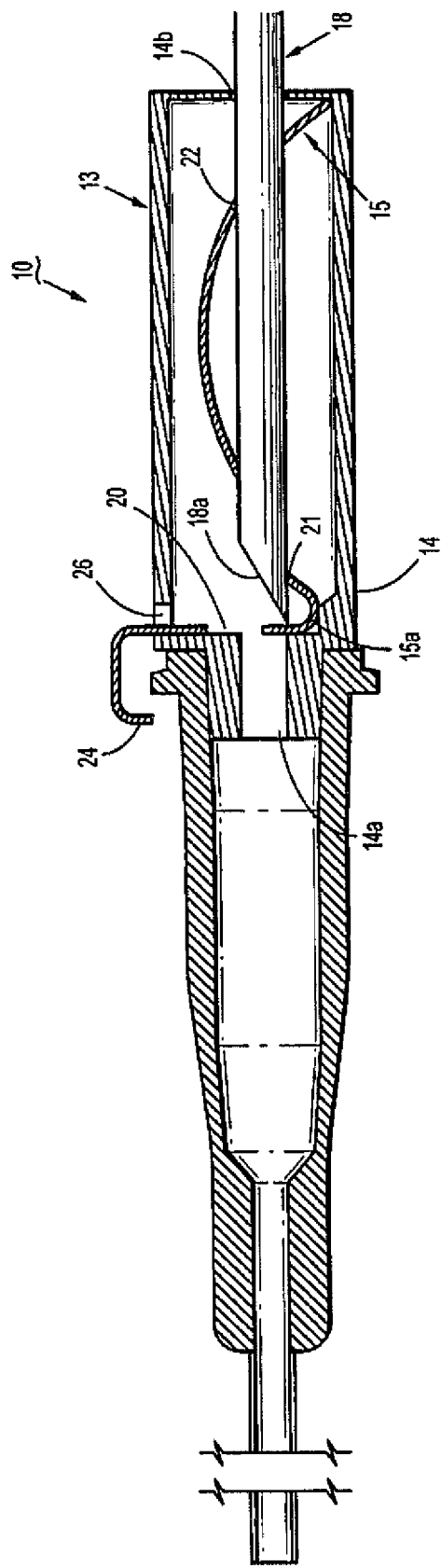
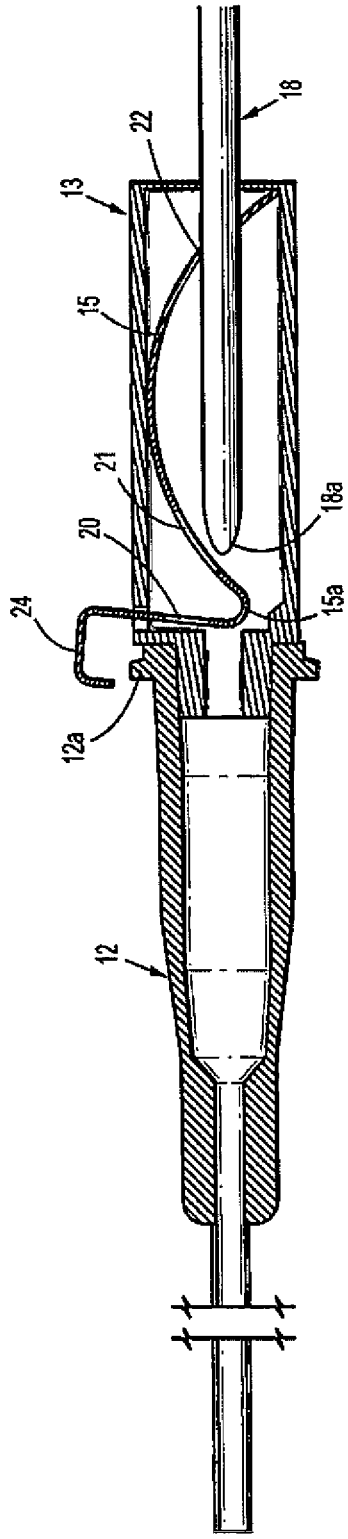
FIG. 3
FIG. 4 ued States Patent No. US 8,591,467 B2

VASCULAR ACCESS ASSEMBLY AND SAFETY DEVICE

RELATED APPLICATIONS

This application claims priority under 35 U.S.C. §119 to U.S. Provisional Application Ser. No. 61/511,187 entitled VASCULAR ACCESS ASSEMBLY WITH SAFETY DEVICE, filed Jul. 25, 2011, the entire contents of which are incorporated herein by reference for all purposes.

BACKGROUND

1. Technical Field

The present disclosure relates to vascular access assemblies, and more particularly to vascular access assemblies including a safety device for protecting a clinician from accidental needle stick injuries.

2. Background

Vascular access assemblies are utilized in a variety of medical applications for supplying or withdrawing fluid to or from a body vessel. Generally, vascular access assemblies include an external cannula for indwelling in a blood vessel of a patient and an internal needle that is inserted into the external cannula to facilitate piercing of the blood vessel of the patient. In operation of the access assembly, the internal needle is inserted into the external cannula such that the tip portion of the internal needle protrudes from a tip portion of the external cannula. Next, the internal needle is manipulated to pierce a blood vessel and to position the external cannula within the blood vessel. While the external cannula is positioned within in the blood vessel, the internal needle is withdrawn from the external cannula leaving the external cannula positioned within the blood vessel. In this position, a medical device can be connected to the rear end portion of the external cannula using, for example, a luer connector, to facilitate the supply and withdrawal of fluid, such as blood, medication and/or nutrients to or from the body vessel.

After the internal needle is withdrawn from the external cannula, the exposed needle tip of the internal needle creates a danger of accidental needle stick injury which can leave a clinician vulnerable to the transmission of various blood-borne pathogens, such as HIV and hepatitis. While needle tip protectors have been developed to protect the clinician from needle stick injuries, the cost, ease of use, and effectiveness of these needle tip protectors leaves room for improvement.

Accordingly, it would be beneficial to provide a vascular access assembly which is easily activated by a clinician, effectively protects a clinician from accidental needle stick injury and is economical to produce.

SUMMARY

A vascular access assembly and safety device is disclosed that includes a catheter assembly including a catheter hub and a catheter tube extending distally from the catheter hub, a needle assembly including a needle having a needle tip, and a safety device including a housing and a safety clip. The housing defines a cavity and proximal and distal openings through endwalls of the housing and the safety clip is formed of a resilient material and is supported within the cavity of the housing. The safety clip defines a distal opening, a central opening and a proximal opening which are aligned with each other and with the proximal and distal openings of the housing in a first deformed position of the safety clip to slidably receive the needle. The needle retains the safety clip in the first deformed position. The housing defines a ramp positioned between the endwalls of the housing and against which the safety clip abuts when the safety clip is in the first deformed position. When the needle is withdrawn from the catheter assembly such that the needle tip passes through the distal opening of the safety clip, the safety clip is configured to ride up the ramp and move to a second position to obstruct distal movement of the needle tip into the distal opening of the housing.

In one embodiment, a distal end of the safety clip includes a hook portion which is positioned to engage the catheter hub when the safety clip is in the first deformed position to releasably secure the safety device to the catheter hub. The hook portion is movable to a position disengaged from the catheter hub when the safety clip moves to the second position.

In one embodiment, the safety clip is configured to move to a third position when the needle tip is withdrawn through the central opening of the safety clip to further obstruct distal movement of the needle tip through the distal opening. In the third position, the orientation of the proximal opening is such that the clip binds with the needle adjacent the third opening to obstruct proximal movement of the needle in relation to the safety clip.

In another embodiment, vascular access assembly and safety device includes a catheter assembly including a catheter hub and a catheter tube extending distally from the catheter hub, a needle assembly including a needle hub and a needle extending distally from the needle hub, and a safety device including a housing defining a cavity and a safety clip supported within the cavity. The housing includes a proximal opening dimensioned to slidably receive the needle and an open distal end. The safety clip has a pair of resilient legs which are configured to releasably engage a proximal end of the catheter hub in a deformed first position of the safety clip to releasably secure the safety device to the catheter assembly. The safety clip is movable to a second non-deformed position, wherein the resilient legs block distal movement of the needle from within the housing.

In one embodiment, each resilient leg of the pair of resilient legs includes a protrusion which is configured to be received in a recess formed in the catheter hub to releasably secure the safety device to the catheter hub. The safety is manually releasable from engagement with the catheter hub.

The safety clip may include a proximal wall defining an opening for slidably receiving the needle. The needle defines an enlarged diameter portion wherein the outer diameter of the enlarged diameter portion is greater than the inside diameter of the opening in the proximal wall of the safety clip such that withdrawal of the needle through the proximal opening of the safety clip is prevented.

In one embodiment, each of the resilient legs of the pair of resilient legs includes a radial portion. The radial portions are dimensioned to obstruct distal movement of the needle when the safety clip is disengaged from the catheter hub and moves from the first deformed position to the second non-deformed position.

In another embodiment, the vascular access assembly and safety device includes a catheter assembly including a catheter hub and a catheter tube extending distally from the catheter hub, a needle assembly including a needle hub and a needle extending distally from the needle hub, the needle including a needle tip, and a safety device including a housing defining a cavity and a safety clip positioned within the cavity. The housing defines a proximal opening and a distal opening. The safety clip is formed from a resilient material and has a U-shaped configuration including a first leg positioned adjacent an inner wall of the housing and a second leg supporting a tab. In an assembled state, the needle extends through the distal and proximal openings of the housing of the safety device and through the catheter assembly and the safety clip is compressed between the inner wall of the housing and the tab slidably engages the needle. Upon withdrawal of the needle tip into the housing of the safety device and proximally of the tab of the safety clip, the safety clip moves to a non-compressed position such that the tab obstructs distal movement of the needle into the distal opening of the housing.

In one embodiment, the needle includes an enlarged diameter portion and a bushing is slidably supported on the needle proximally of the enlarged diameter portion. The inner diameter of the bushing is smaller than the outer diameter of the enlarged diameter portion, and the outer diameter of the bushing is larger than the inner diameter of the proximal opening of the housing of the safety device to prevent withdrawal of the needle tip from the proximal opening.

The housing may include a resilient arm which includes a projection which is received in a recess formed in the catheter hub to releasably secure the catheter hub to the safety device.

In one embodiment, the tab if the safety clip includes a rounded end portion positioned to slidably engage the needle in the assembled state.

In another embodiment, the vascular access assembly and safety device includes a needle having a needle tip and an enlarged diameter portion, and the safety device includes a housing defining a throughbore and having a distal open end and a proximal opening dimensioned to slidably receive the needle. The housing includes a resilient arm including a radially extending protrusion configured to releasably engage a catheter hub. A first disk is fixedly supported within the housing and defines a recess defined by a plurality of proximally extending fingers. The proximally extending fingers define a central opening and are configured to deflect inwardly to facilitate passage of the enlarged diameter portion of the needle in a proximal direction through the central opening of the disk but to prevent passage of the enlarged diameter portion of the needle through the central opening of the disk in a distal direction.

In one embodiment, the safety device recess is frustoconical or spherical.

The safety device may further include a second disk supported proximally of the first disk. The second disk includes a plurality of distally extending fingers that define a central opening and are configured to prevent passage of the enlarged diameter portion of a needle in the proximal direction.

In another embodiment, the vascular access assembly and safety device includes a needle including an enlarged diameter portion and a needle tip, a housing defining a cavity having an open distal end and a proximal opening, a large diameter portion, a small diameter portion, a distally facing ramp portion positioned between the large diameter portion and the small diameter portion, and a proximally facing shoulder positioned adjacent a proximal end of the ramp portion. A clip which is formed of a resilient material and has a proximal wall defining an opening for slidably receiving a needle is provided. A leg extends radially outwardly and distally from each end of the proximal wall. Each leg includes a radially and proximally extending portion. At least one of the radially and proximally extending portions includes a cutout for slidably receiving the needle. In an advanced position of the needle, the clip is positioned about the needle in the large diameter portion of the housing and the needle extends distally from the open distal end of the housing. Upon withdrawal of the needle tip into the housing, the enlarged diameter portion of the needle engages the radially and proximally extending portions to deflect the radially and proximally extending portions inwardly to allow passage of the enlarged diameter portion of the needle past the radially and proximally extending portions and into engagement with the proximal wall. Further withdrawal of the needle effects movement of the clip over the distally facing ramp portion, past the proximally facing shoulder and into the small diameter portion of the cavity. The enlarged diameter portion of the needle has a diameter larger than the opening in the proximal wall to prevent proximal movement of the needle tip from a proximal end of the housing. The small diameter portion of the cavity of the housing prevents outward deflection of the radially and proximally extending portions of the clip and the proximally facing shoulder prevents distal movement of the clip from the small diameter portion to prevent distal movement of the needle tip from the cavity of the housing.

BRIEF DESCRIPTION OF THE DRAWINGS

Various embodiments of the presently disclosed vascular access assembly and safety device will be described herein with references to the accompanying drawings, wherein:

FIG. 3 is a side cross-sectional view of the vascular access assembly and safety device shown in FIG. 2 with the needle withdrawn into the housing of the safety device through the distal opening of the safety clip;

FIG. 4 is a side cross-sectional view of the vascular access assembly and safety device shown in FIG. 2 with the needle tip withdrawn into the housing of the safety device through the central opening of the safety clip;

DETAILED DESCRIPTION OF EMBODIMENTS

Figure 1:
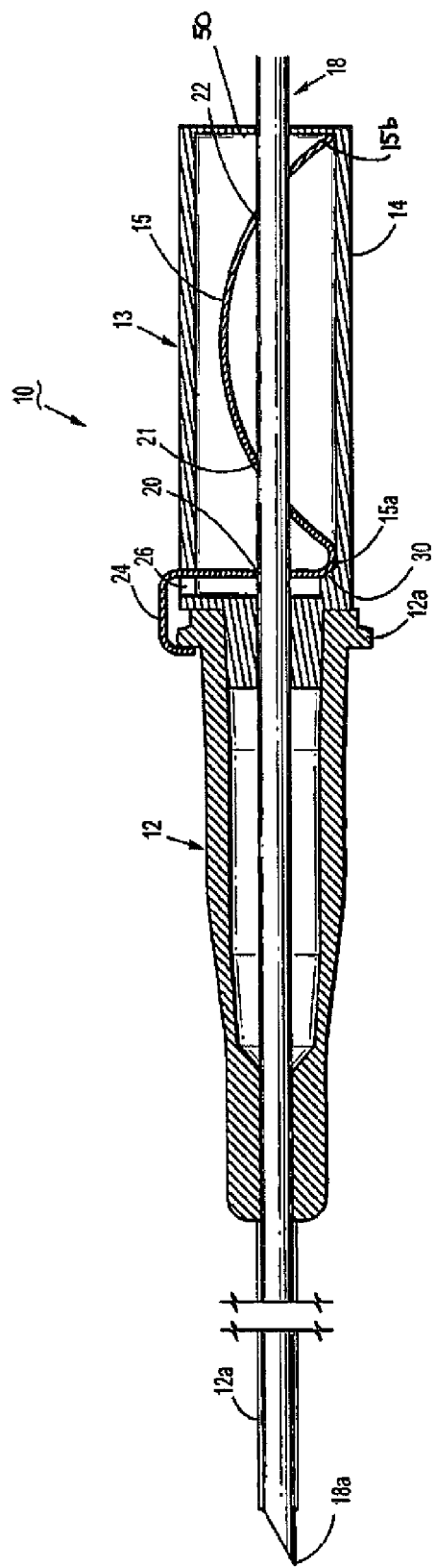
FIG. 1 is a side cross-sectional view of one embodiment of the presently disclosed vascular access assembly and safety device with the needle in an advanced position.

Embodiments of the presently disclosed vascular access assembly and safety device will now be described in detail with reference to the drawings wherein like reference numerals designate identical or corresponding elements in each of the several views. In this description, the term "proximal" is generally used to refer to the portion of the device that is closer to a clinician, while the term "distal" is generally used to refer to the portion of the device that is farther from the clinician. As used herein, the term "patient" should be understood as referring to a human patient or other animal, and the term "clinician" should be understood as referring to a doctor, nurse or other care provider and may include support personnel.

Figure 2:
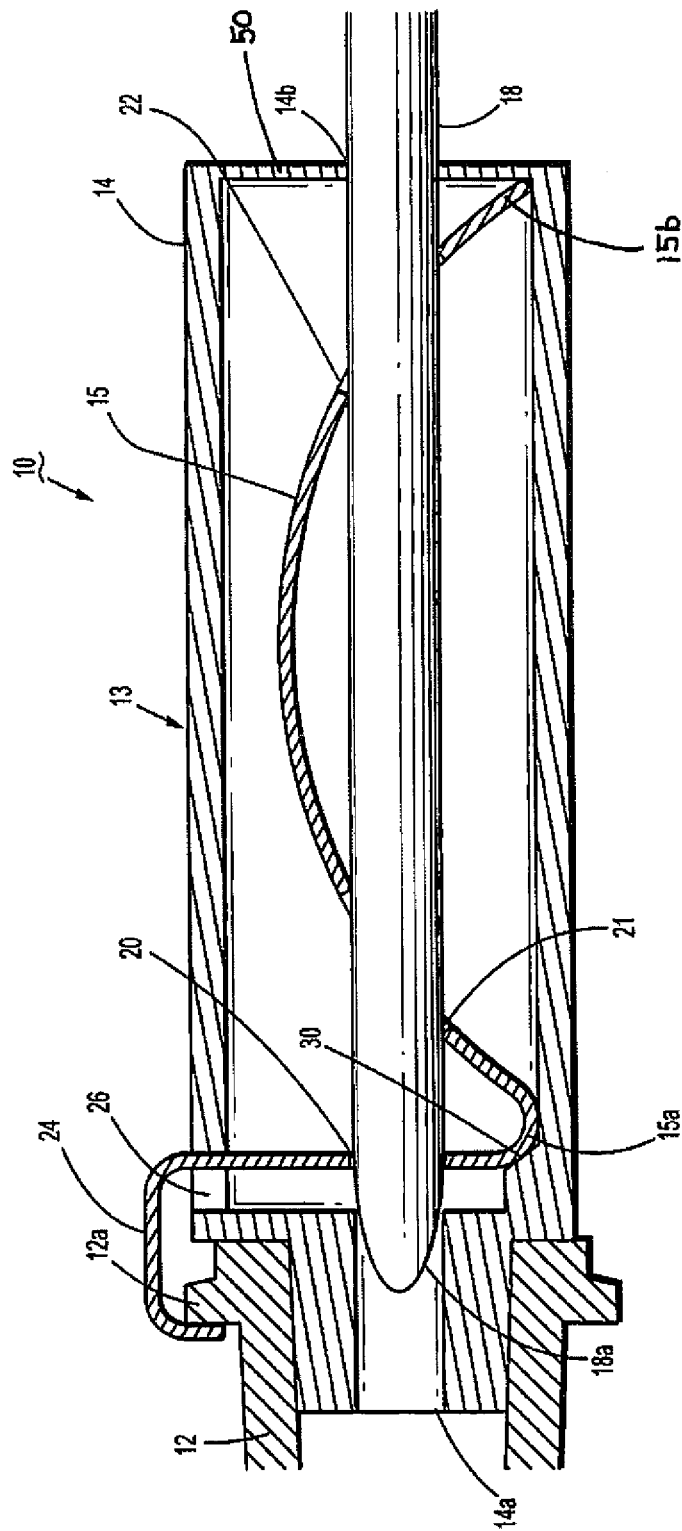
FIG. 2 is an enlarged view of the safety device and proximal end of the catheter hub of the vascular access assembly shown in FIG. 1 with the needle tip about to enter the housing of the safety device.

FIGS. 1-3 illustrate one embodiment of the presently disclosed vascular access assembly and safety device, hereinafter access assembly, shown generally as 10. Access assembly 10 comprises a catheter assembly including a catheter hub 12 (FIG. 1) and a catheter tube 12a, a safety device 13 having a housing 14 and a safety clip 15 supported within the housing 14, and a needle assembly including a needle 18 and a needle hub (not shown). In a ready to use position, shown in FIG. 1, the needle 18 extends from the needle hub, through distal and proximal openings 14a and 14b (FIG. 2), respectively, in the safety device housing 14, and through catheter hub 12 and catheter tube 12a of the catheter assembly.

As shown in FIGS. 1-3, the safety clip 15 is formed from a substantially flat, resilient member which includes a distal opening 20, a central opening 21, and a proximal opening 22. In one embodiment, the safety clip 15 is formed from spring steel. Alternately, other resilient materials can be used to form the safety clip 15. In the ready-to-use position or assembled state, the needle 18 is positioned to extend through the distal, central, and proximal openings 20-22, respectively, of the safety clip 15, to retain the safety clip 15 in a curved, deformed configuration within the housing 14. In this configuration, holes 20-22 of safety clip 15 are aligned with distal and proximal openings 14a and 14b of safety device housing 14 and oriented to allow the needle to be withdrawn from the catheter assembly through the safety clip 15.

A distal end of the safety clip 15 includes a hook portion 24 which extends through an opening 26 in the housing 14. In the ready-to-use position of the access assembly 10, the proximal, central, and distal openings 20-22 of the safety clip 15 are aligned with the openings 14a and 14b of the housing 14 and the hook portion 24 of safety clip 15 is engaged with a luer connector 12a of the catheter hub 12 to releasably secure the housing 14 to the proximal end of the catheter hub 12. In addition, a proximal end 15b of safety clip 15 abuts endwall 50 of housing 14. See FIG. 5.

Referring to FIG. 2, an inner wall of housing 14 defines a ramp 30 which abuts a portion 15a of safety clip 15 between distal and central openings 20 and 21. The ramp 30 prevents distal expansion of safety clip 15 in the ready-to-use position of the assembly 10 to retain hook portion 24 of safety clip 15 in contact with catheter hub 12.

Figure 5:
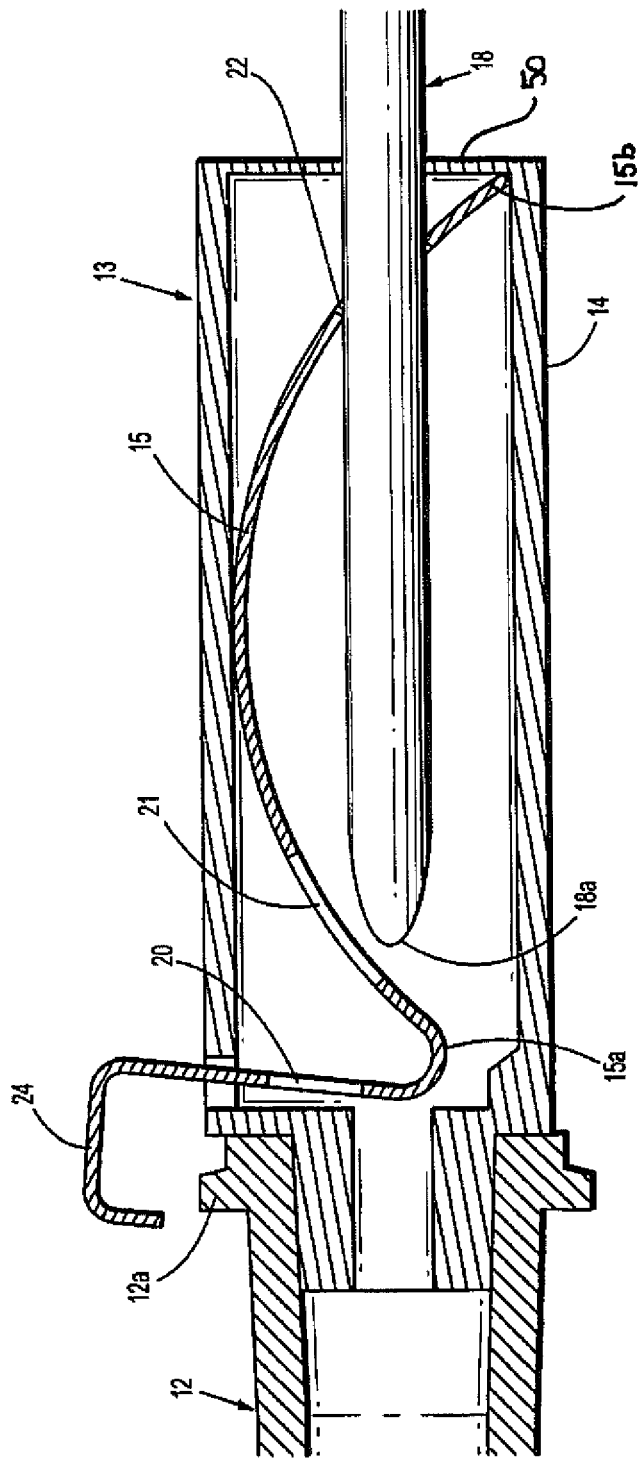
FIG. 5 is an enlarged view of the safety device and proximal end of the catheter hub of the vascular access assembly and safety device shown in FIG. 1 after the needle tip has been withdrawn into housing of the safety device and through the distal and central openings of the safety clip.

Referring to FIGS. 3-5, when the needle 18 is retracted such that the needle tip 18a passes through distal opening 20 of safety clip 15, the distal end of the safety clip 15, which is no longer constrained by the needle 18, expands outwardly and upwardly within housing 14. When this occurs, the portion 15a of safety clip 15 defined between distal and central openings 20 and 21 rides up ramp 30 of housing 14 to lift hook portion 24 from engagement with catheter hub 12 and to partially cover or obstruct distal opening 14a of housing 14. See FIG. 3. This prevents distal advancement of needle 18 from housing 14 of safety clip 15. Concurrently, safety clip 15 tends to flatten. As the tip 18a of the needle 18 is withdrawn through central opening 21, safety clip 15 flattens to change the orientation of opening 22 with respect to needle 18. This change in orientation causes proximal opening 22 of safety clip 15 to tilt with respect to the longitudinal axis of needle 18 such that the edge of clip 15 defining opening 22 engages needle 18 to prevent further retraction of needle 18 through housing 14. Thus, tip 18a of needle 18 is safely retained within housing 14 of the safety device 15. See FIG. 5. As shown in FIGS. 4 and 5, when needle tip 18a passes through central opening 21 of safety clip 15, safety clip 15 expands outwardly and upwardly within housing 14 to block distal opening 14a.

Figure 6:
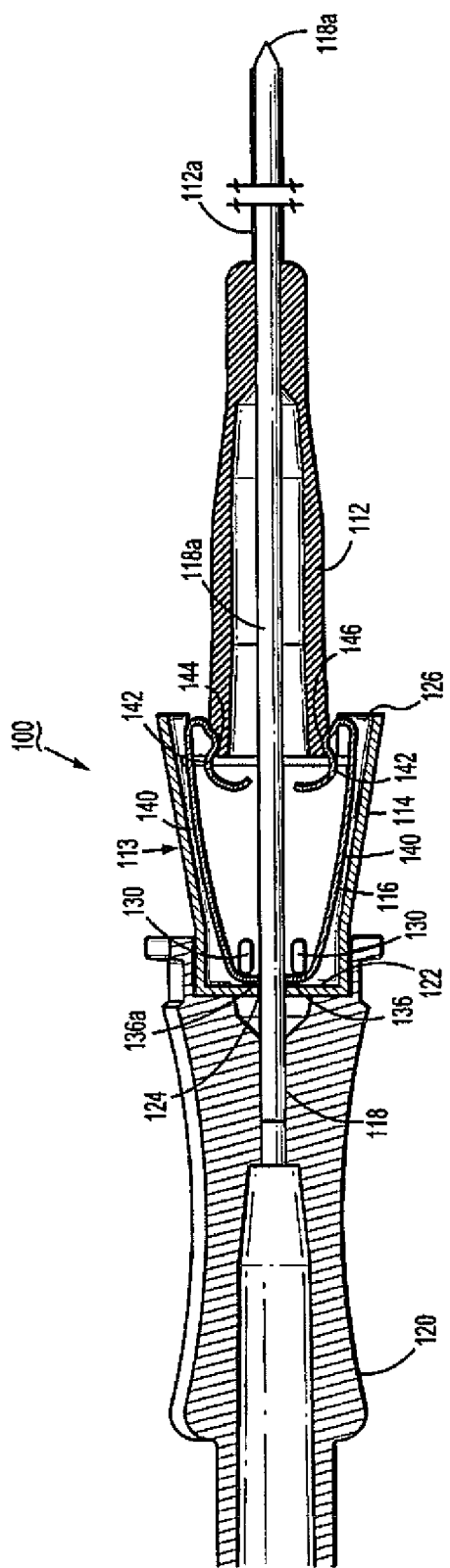
FIG. 6 is a side cross-sectional view of another embodiment of the presently disclosed vascular access assembly and safety device in an assembled state.
Figure 7:
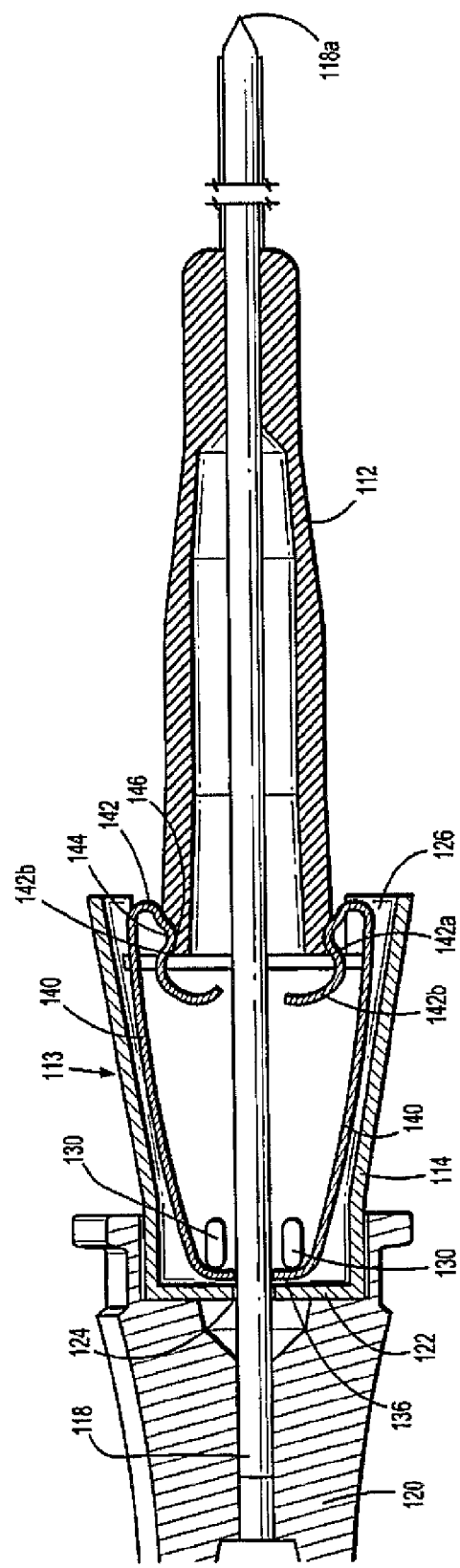
FIG. 7 is an enlarged side cross-sectional view of the vascular access assembly and safety device shown in FIG. 6.
Figure 8:
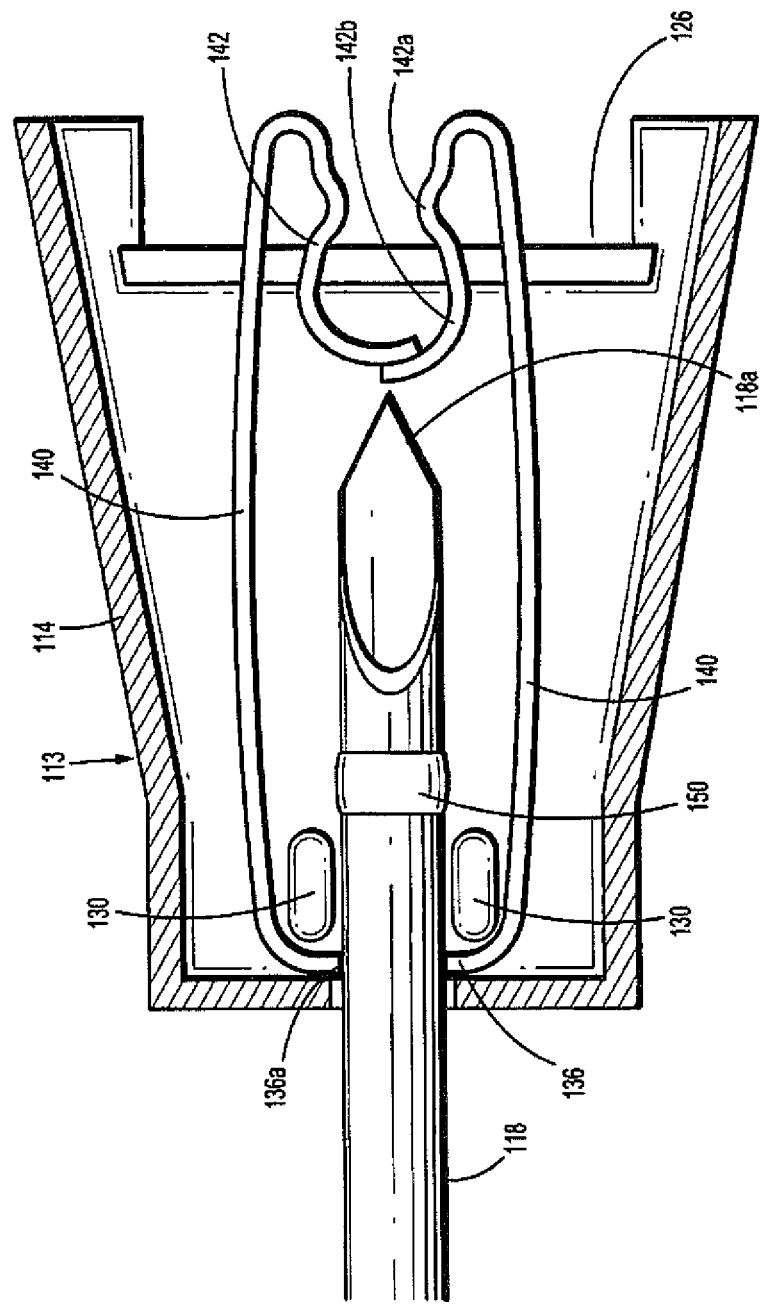
FIG. 8 is a side, cross-sectional view of the safety device and needle shown in FIG. 7 with the safety clip disengaged from the catheter hub.

FIGS. 6-8 illustrate another embodiment of the presently disclosed access assembly shown generally as 100. Access assembly 100 includes a catheter assembly having a catheter hub 112 and a catheter tube 112a extending distally of the catheter hub 112, a safety device 113 including a housing 114 and a safety clip 116, and a needle assembly including a needle 118 and a needle hub 120 supporting a proximal end of the needle 118. The needle 118 includes a sharpened tip 118a. In a ready-to-use position, the needle 118 extends through the safety device 113 and the catheter assembly such that the tip 118a of needle 118 extends from a distal end of the catheter tube 112a.

Referring to FIGS. 6 and 7, safety clip 116 is received within a cavity 114a housing 114. Housing 114 includes a proximal wall 122 defining an opening 124 for slidably receiving needle 118 and an open distal end 126. A pair of spaced posts 130 are formed in housing 114 for fixedly locating the safety clip 116 within the housing 114 as will be discussed below.

Safety clip 116 includes a proximal wall 136 defining an opening 136a for slidably receiving the needle 118. A resilient leg 140 extends distally from each end of proximal wall 136. The distal end of each leg 140 supports a substantially L-shaped member 142 (FIG. 8) which includes a longitudinal portion 142a and a radial portion 142b (FIG. 7). The longitudinal portion 142a of each L-shaped member 142 includes a protrusion 144 which is positioned to be received in a recess 146 formed in a proximal end of catheter hub 112 to releasably secure catheter hub 112 to safety clip 116 when the access assembly 100 is in the ready-to-use position. In the ready-to-use position of access assembly 100, members 142 are spaced from needle 118 to minimize drag on the needle 118. The radial portions 142b are dimensioned to overlap (FIG. 8) when the needle tip 118a of needle 118 is retracted into housing 114 of safety device 113 as will be discussed below. Alternately, the radial portions 142b need not overlap but should be configured to prevent distal movement of the needle 118 when the safety clip 116 moves to a non-deformed configuration.

Referring to FIG. 8, needle 118 includes an enlarged diameter portion 150, which may be formed by providing a crimp in needle 118. Alternatively, enlarged diameter portion 150 may be formed in a variety of different ways including providing an annular protrusion about needle 118 by welding or the like. Enlarged diameter portion 150 has an outer diameter larger than the inner diameter of opening 136a formed in proximal wall 136 of clip 116. When needle 118 is withdrawn into safety clip housing 114, enlarged diameter portion 150 engages proximal wall 136 and pulls safety clip 116 (and housing 114) proximally in relation to catheter hub 112 (FIG. 7), which is held stationary by a clinician. As clip 116 is pulled proximally in relation to catheter hub 112, resilient legs 140 of clip 116 flex outwardly as protrusions 144 are manually disengaged from recesses 146 (FIG. 6) of catheter hub 112. When legs 140 move proximally over the proximal end of catheter hub 112, legs 140 return to their non-deformed configuration, wherein radial portions 142b of legs 140 overlap and/or block distal movement of needle 118.

Figure 9:
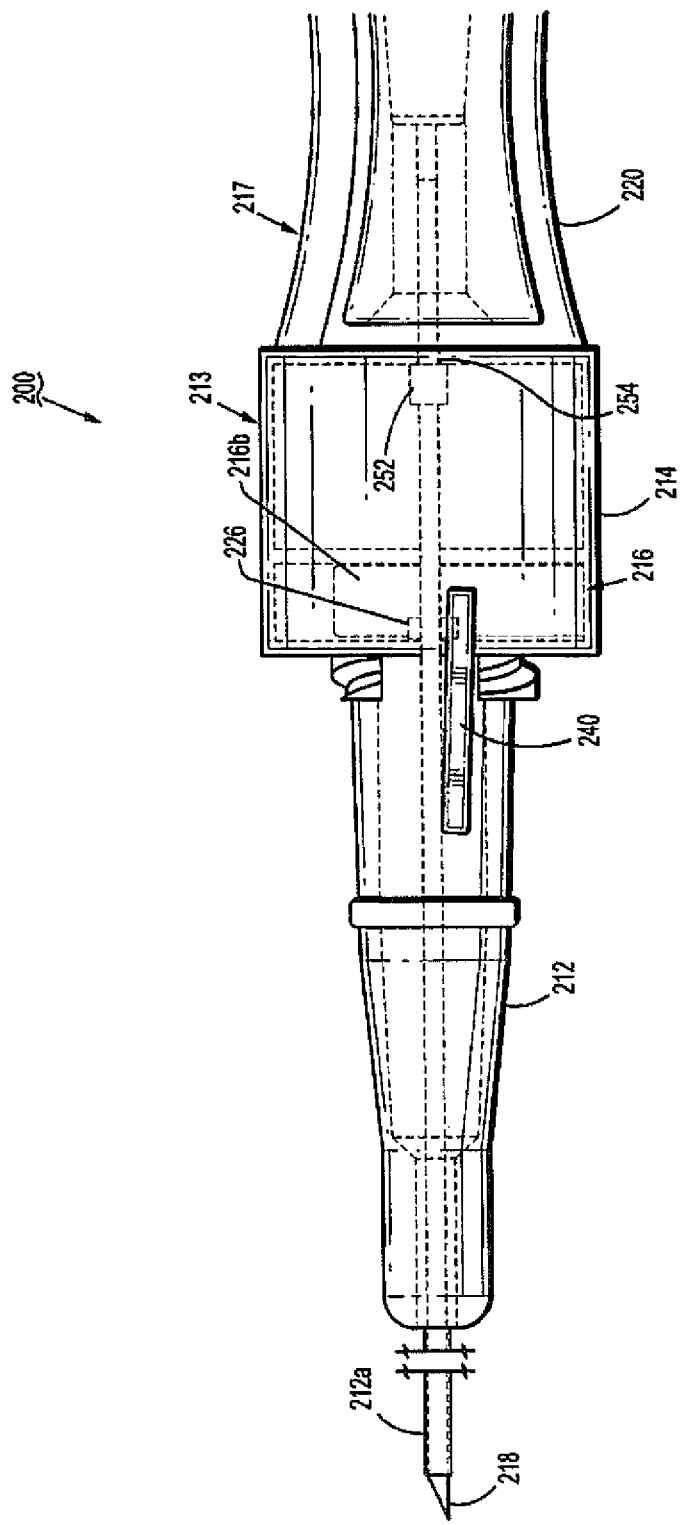
FIG. 9 is a side view of another embodiment of the presently disclosed vascular access assembly and safety device in an assembled state.
Figure 10:
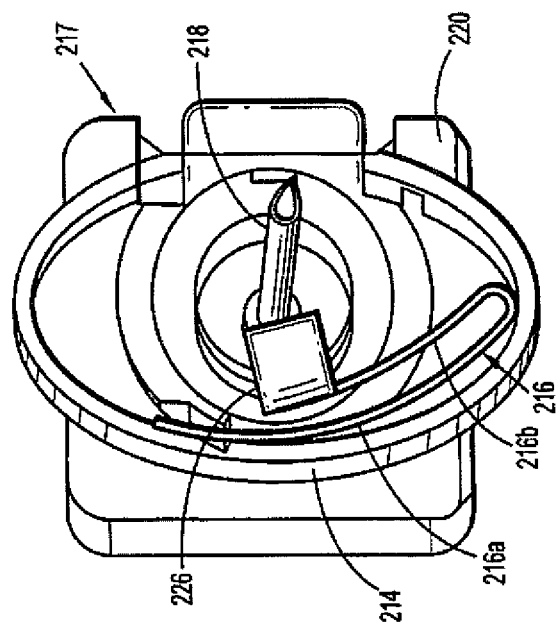
FIG. 10 is a cutaway view through the housing of the safety device looking proximally into the housing.

FIGS. 9-12 illustrate another embodiment of the presently disclosed access assembly shown generally as 200. Access assembly 200 comprises a catheter assembly including a catheter hub 212 and a catheter tube 212a, a safety device 213 including a housing 214 and a safety clip 216, and a needle assembly 217 including a needle 218 and a needle hub 220. Housing 214 defines a distal opening 238 and a proximal opening 254. In the ready-to-use position of access assembly 200, needle 218 extends through housing 214 of safety device 213 and catheter hub 212 of catheter assembly such that a needle tip 218a of needle 218 extends from a distal end of the catheter tube 212a (FIG. 9).

Safety clip 216 is supported in housing 214 and has a curved U-shaped configuration (FIG. 10) having a first leg 216a and a second leg 216b. In the ready-to-use position, the first leg 216a is positioned adjacent an inner wall of housing 214 and the second leg 216b is positioned between the first leg 216a and the needle 218. Alternately, other configurations are envisioned. Safety clip 216 is formed from a resilient material such as spring steel and includes a radially extending tab 226 supported on second leg 216b. In the ready-to-use position of access assembly 200, the second leg 216b is deflected towards the first leg 216 by engagement of radially extending tab 226 with needle 218. More specifically, the safety clip 216 is compressed between an inner wall of housing 214 and the needle 218 via engagement of tab 226 with needle 218. In one embodiment, the tab 226 includes rounded end portion 226a (FIG. 12) positioned to slidably engage the needle 218.

Housing 214 of safety device 213 includes a resilient arm 240 having a distal projection 240a which is received in a recess 242 formed in an outer wall of catheter hub 212 to releasably secure the safety device 216 to the catheter hub 212. See FIG. 11.

Figure 11:
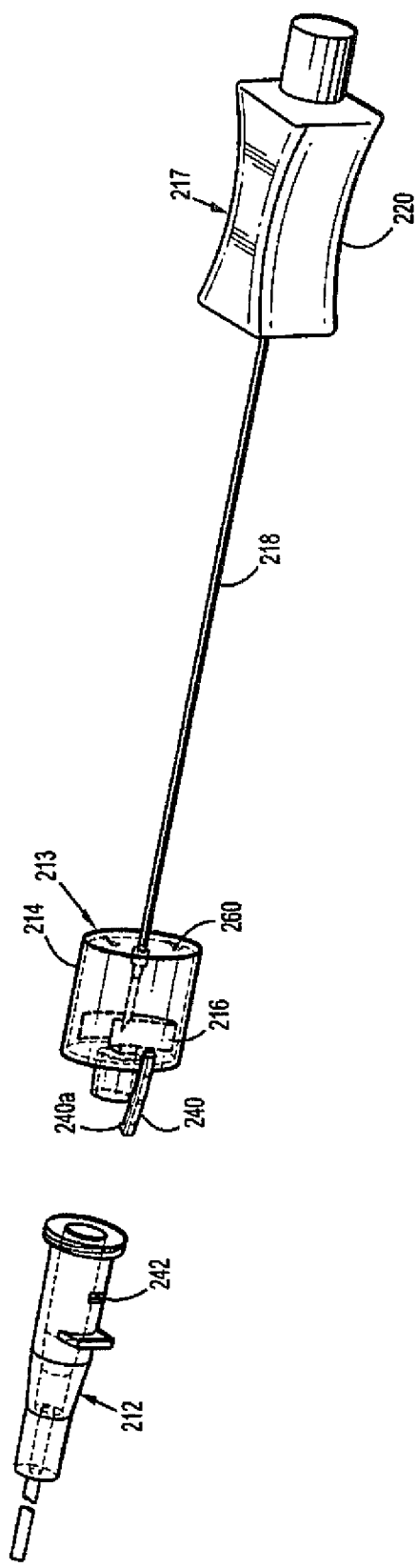
FIG. 11 is a perspective view with parts separated of the vascular access assembly and safety device shown in FIG. 9 with the needle tip withdrawn into the housing of the safety device.
Figure 12:
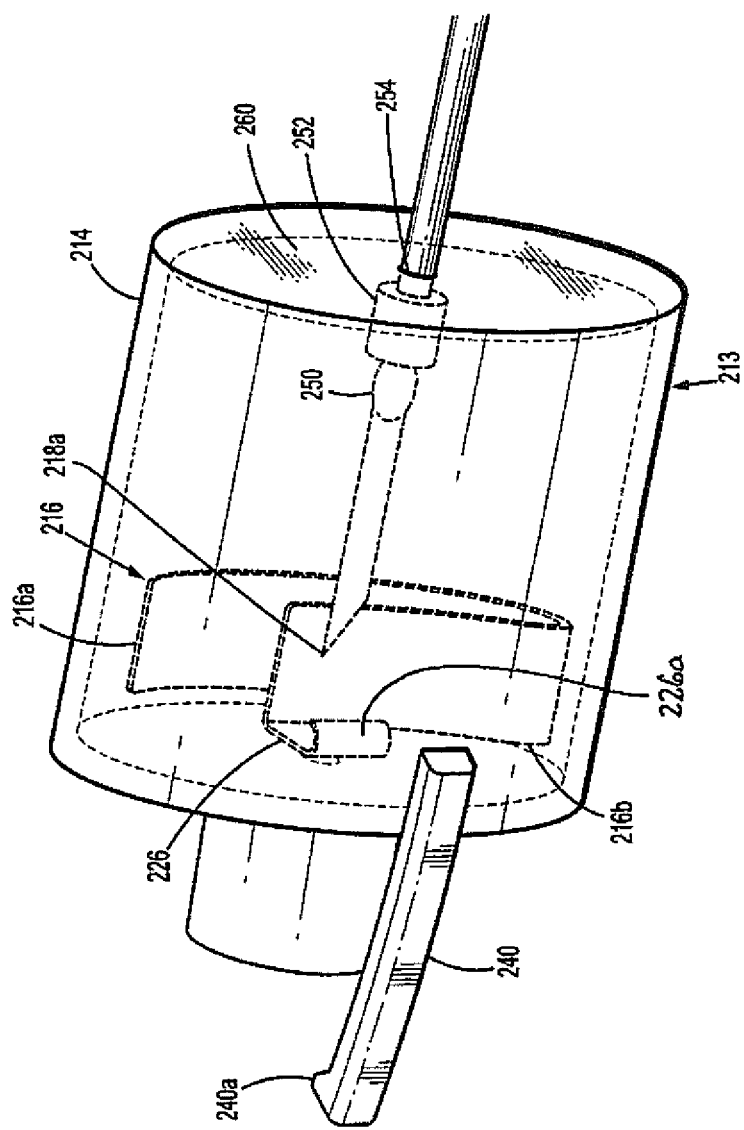
FIG. 12 is an enlarged view of the safety device shown in FIG. 11 supported on the distal end of the needle with the distal end of the needle and safety clip shown in phantom.
Figure 13:
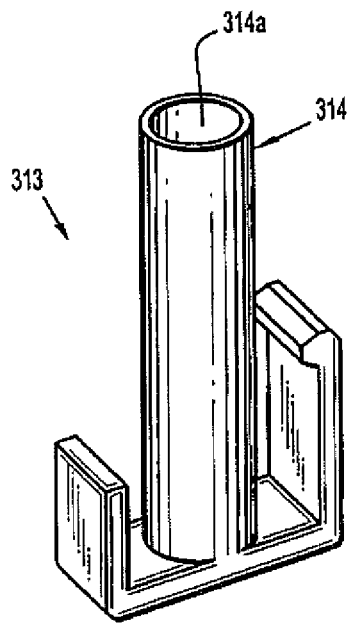
FIG. 13 is a perspective view of another embodiment of a safety device for use with a vascular access assembly.

Referring to FIGS. 11 and 12, needle 218 includes an enlarged diameter portion 250. In addition, a bushing 252 is slidably positioned about needle 218 proximally of enlarged diameter portion 250. Bushing 252 has an inside diameter smaller than the outside diameter of enlarged diameter portion 250 and an outside diameter which is larger than the inside diameter of the opening 254 in the proximal end of housing 214. When the needle 218 is retracted into housing 214 of safety clip 216 and needle tip 218a passes proximally of radially extending tab 226, second leg 216b of clip 216 moves towards a non-deformed or non-compressed position wherein tab 226 moves to a position in front of and distally of needle tip 218a to prevent distal movement of needle tip 218 from housing 214. See FIG. 12. Proximal retraction of needle tip 218a from housing 214 is prevented by engagement of enlarged diameter portion 250 of needle 218 with bushing 252 and subsequently, by engagement of bushing 252 with a proximal wall 260 of housing 214. See FIG. 12.

Figure 14:
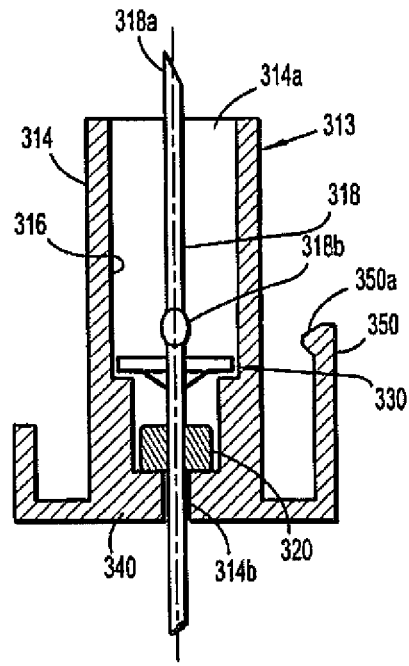
FIG. 14 is a side cross-sectional view of the safety device shown in FIG. 13 with a needle of the vascular access assembly extending through the safety device.

FIGS. 13-15B illustrate an alternate embodiment of the presently disclosed safety device shown generally as 313. Safety device 313 includes a housing 314 having a distal open end 314a and a proximal opening 314b (FIG. 14). Housing 314 defines a throughbore 316 for slidably receiving a needle 318 having a sharpened tip 318a and an enlarged diameter portion 318b. A bushing 320 is positioned about the needle 318 at a location proximal of the enlarged diameter portion 318b. The bushing 320 has an inside diameter smaller than the outside diameter of the enlarged diameter portion 318b, and an outside diameter portion larger than the inside diameter portion of the proximal opening 314b of housing 314. A disk 330 includes a plurality of proximally angled spring fingers 332 (FIGS. 15A-15B) positioned about a central opening 334 and is secured to an inner wall of housing 314.

In use, due to the orientation of spring fingers 332, when needle 318 is retracted within housing 314, fingers 332 will deflect inwardly upon engagement with enlarged diameter portion 318b of needle 318 to allow enlarged diameter portion 318b to pass through central opening 334 of disk 330. In this position, with enlarged diameter portion 318b positioned between disk 330 and bushing 320, the needle tip 318a is positioned safely within housing 314. Continued distal movement of needle 318 with respect to housing 314 is prevented by engagement of enlarged diameter portion 318b of needle 318 with fingers 332 of disk 330 and continued proximal movement or withdrawal of needle 318 from housing 314 is prevented by engagement of enlarged diameter portion 318b of needle 318 with bushing 320 and subsequently by engagement of bushing 320 with a proximal wall 340 of housing 314.

Figure 15A:
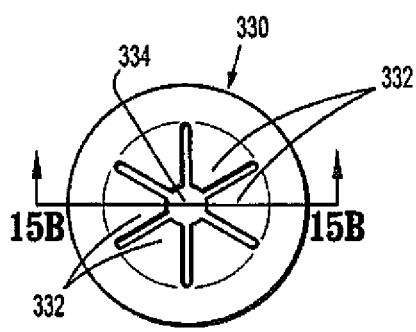
FIG. 15A is a top view of a disk of the safety device shown in FIG. 14.
Figure 16A:
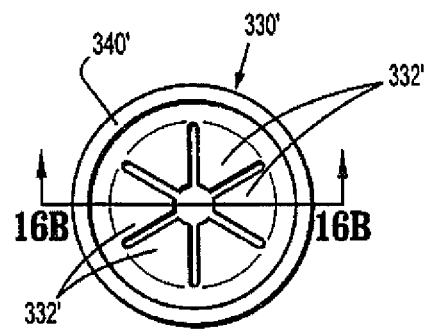
FIG. 16A is a top view of another embodiment of a disk of the safety device shown in FIG. 14.
Figure 15B:
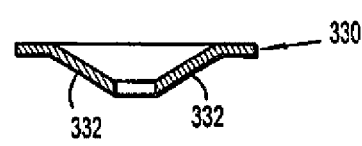
FIG. 15B is a cross-sectional view taken along section line 15B-15B of FIG. 15A.
Figure 16B:
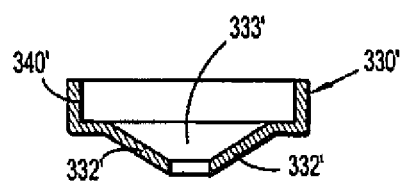
FIG. 16B is a cross-sectional view taken along section lines 16B-16B of FIG. 16A.

Referring to FIGS. 15A-15B, disk 330 may be formed from a resilient material such as spring steel. In one embodiment, fingers 332 of disk 330 are planar and define a frustaconical recess. In an alternative embodiment, such as shown in FIGS. 16A-16B, disk 330' and fingers 332' define a spherical recess 333' and disk 330' includes an annular sidewall 340' positioned about disk 330'.

Although not discussed in detail herein, housing 314 supports a resilient arm 350 including a protrusion 350a for releasably engaging a catheter hub (not shown) in a manner similar to that described above with respect to resilient arm 240 and catheter hub 212. The resilient arm 350 is spaced outwardly of and extends substantially parallel to housing 314

Figure 17:
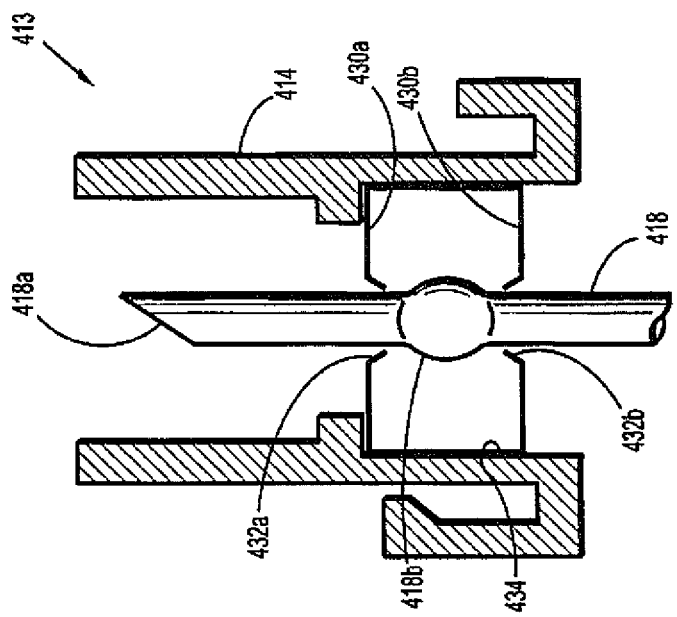
FIG. 17 is a side cross-sectional view of an alternate embodiment of the safety device shown in FIG. 13 with a needle of a vascular access assembly extending therethrough.

In another alternative embodiment of the presently disclosed safety device shown generally in FIG. 17 as 413, two disks 430a and 430b are mounted in housing 414. Disk 430a includes proximally angled fingers 432a and disk 430b includes distally angled fingers 432b. Fingers 432a prevent distal advancement of needle 418 when enlarged diameter portion 418b of needle 418 is positioned between disks 430a and 430b and fingers 432b prevent proximal movement or retraction of needle 418 when enlarged diameter portion 418b is positioned between disks 430a and 430b. In one embodiment, disks 430a and 430b are integrally formed and are connected together by a cylindrical wall 434.

Figure 18A:
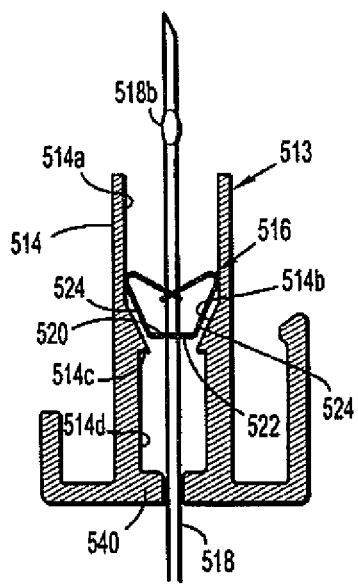
FIG. 18A is a side cross-sectional view of another embodiment of the safety device shown in FIG. 13 with the needle of the vascular access assembly extending through the housing of the safety device.
Figure 18B:
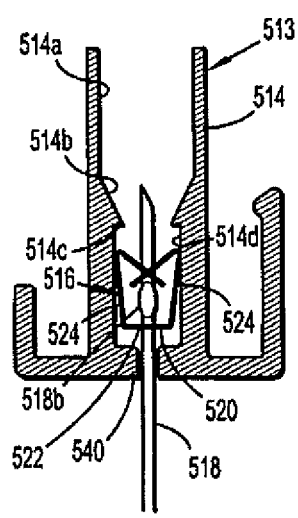
FIG. 18B is a side cross-sectional view of the safety device shown in FIG. 18A with the tip of the needle withdrawn into the housing of the safety device.
Figure 19:
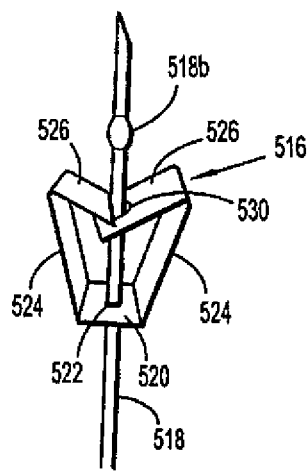
FIG. 19 is a side perspective view of the clip of the safety device shown in FIG. 18A supported on the needle of the vascular access assembly.
Figure 20:
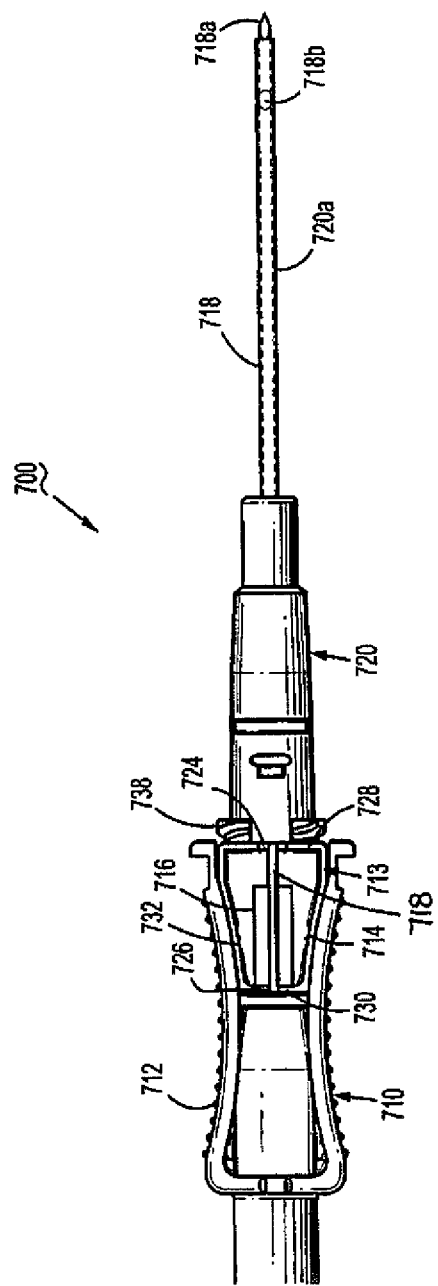
FIG. 20 is a side view of another embodiment of the presently disclosed vascular access assembly and safety device in an assembled state.
Figure 21:
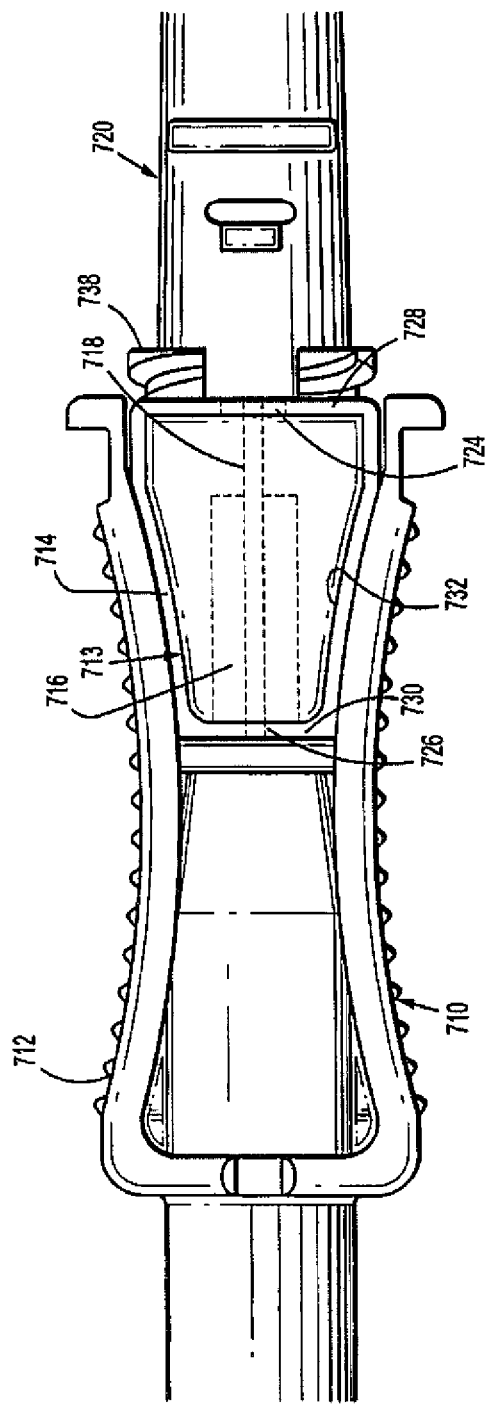
FIG. 21 is a side view of the vascular access assembly and safety device shown in FIG. 20 in an assembled state with the biasing member and needle in the housing of the safety device shown in phantom.

FIGS. 18A-19 illustrate another alternate embodiment of the presently disclosed safety device shown generally as 513. Safety device 513 includes a housing 514, having an inner wall defining a cavity having a large diameter portion 514a, a distally facing ramp portion 514b, a proximally facing shoulder 514c and a small diameter portion 514d. A clip 516 includes a proximal wall 520 defining an opening 522 for slidably receiving a needle 518. Clip 516 is formed from a resilient material, e.g., spring steel, and also includes a leg 524 extending from each side of proximal wall 520. Each leg 524 extends outwardly and distally from proximal wall 520 and includes a radially and proximally extending portion 526 (FIG. 19). One radially extending portion 526 defines a cutout 530 (FIG. 21) for slidably receiving needle 518 therein.

In use, when needle 518 is retracted into housing 514, enlarged diameter portion 518b of needle 518 will engage and deflect radially extending portions 526 of clip 516 inwardly and, subsequently, move into engagement with proximal wall 520 of clip 516. Because enlarged diameter portion 518b has a larger diameter than opening 522, further retraction of needle 518 into housing 514 pulls clip 516 over ramp portion 514b of housing 514 and into the small diameter portion 514d of housing 514 between proximally facing shoulder 514c and a proximal wall 540 of housing 514. See FIG. 18B. In this position, proximal wall 540 of housing 514 prevents retraction of needle 518 from housing 514 and shoulder 514c of housing 514 prevents distal advancement of needle 518 from within small diameter portion 514d. More specifically, the small diameter portion 514d of housing 514 is dimensioned to prevent outward deflection of legs 524 of clip 516. Since legs 524 are prevented from deflecting outwardly, the enlarged diameter portion 518b of needle 518 is prevented from being moved distally past radial portions 526 of legs 524. It is noted that enlarged diameter portion 518b is too large to pass through cutout 530 in radially extending portion 526.

FIGS. 20-23 illustrate another embodiment of the presently disclosed access assembly shown generally as 700. Access assembly 700 comprises a needle assembly 710 including a needle hub 712 supporting a distally extending needle 718, a safety device 713 including a housing 714 and a biasing member 716, and a catheter assembly including a catheter hub 720 and a catheter tube 720a extending distally from the catheter hub 720. In a ready-to-use position, the housing 714 of the safety device 713 is supported between the needle hub 712 and the catheter hub 720 and the needle 718 extends through the safety device housing 714 and the catheter hub 720 such that a tip 718a of needle 718 projects from a distal end of the catheter tube 720a.

The safety clip housing 714 defines a distal opening 724 and a proximal opening 726 and includes a distal wall 728, a proximal wall 730 and sidewalls 732. The biasing member 716 is supported within housing 714 between a sidewall 732 and needle 718. See FIG. 23. In the ready-to-use position of access assembly 700 shown in FIGS. 20-21, needle 718 extends through distal and proximal openings 724 and 726 of housing 714 and includes a tip 718a which extends from catheter tube 720a. In addition, the biasing member 716 is compressed between sidewall 732 and needle 718. Housing 714 also includes a hook portion 734 (FIG. 22) which is engaged with a luer connector 738 of catheter hub 720.

Figure 22:
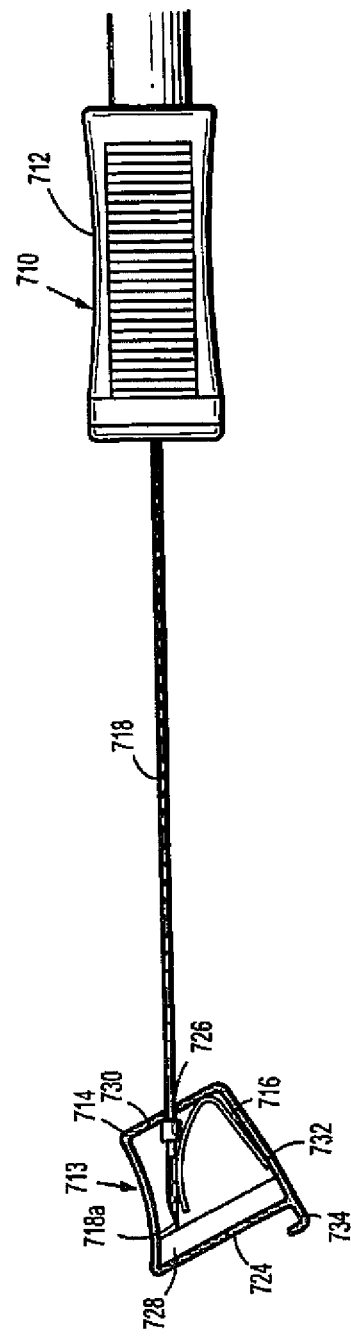
FIG. 22 is a side partial cross-sectional view of the safety device and needle assembly of the vascular access assembly shown in FIG. 20 with the needle tip of the needle assembly withdrawn into the housing of the safety device.
Figure 23:
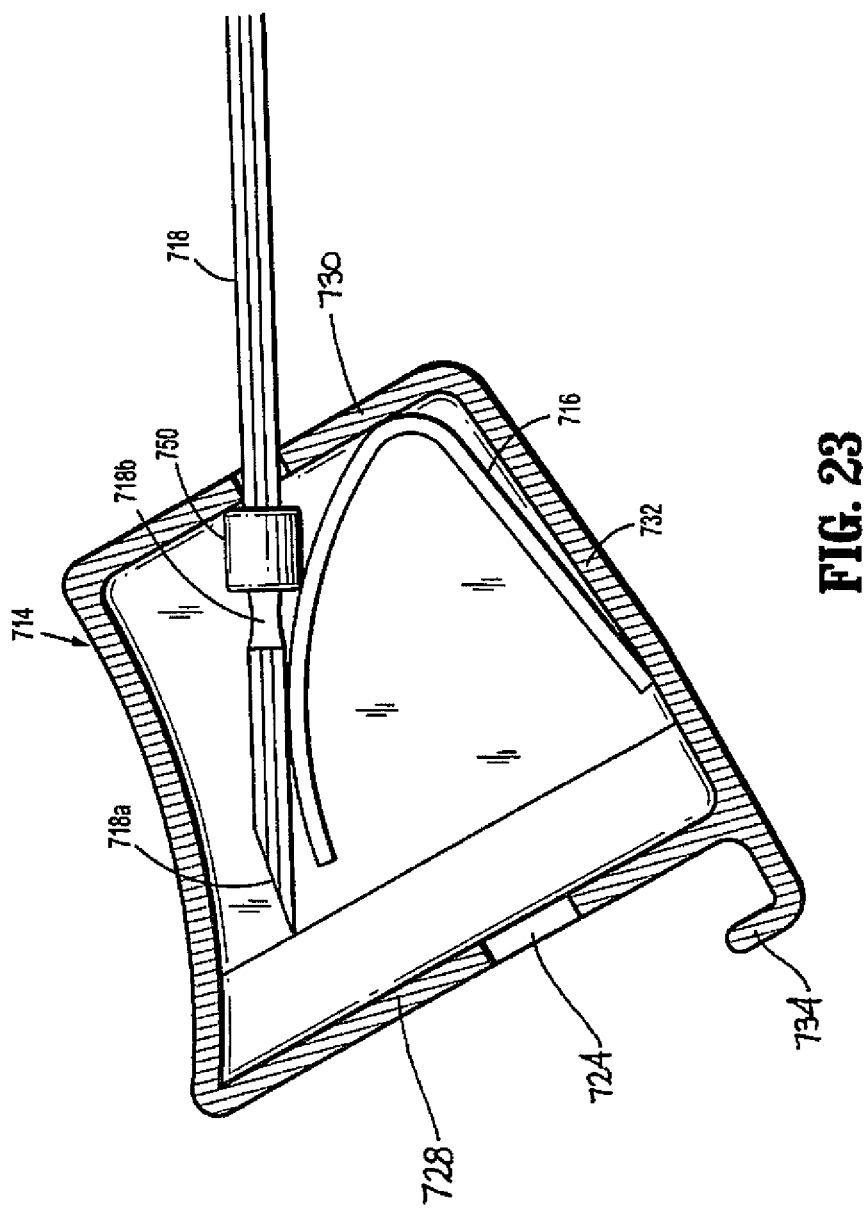
FIG. 23 is an enlarged view of the safety device supported on the distal end of the needle as shown in FIG. 22.

Referring to FIGS. 22-23, when needle 718 is retracted to withdraw tip 718a into housing 714 of safety device 713, biasing member 716 expands towards a non-compressed position to tilt the housing 714 with respect to needle 718. When this occurs, the distal opening 724 of housing 718 becomes misaligned with the longitudinal axis of needle 718 and the needle tip 718a is covered by distal wall 728 of housing 714. During tilting of housing 714, hook portion 734 is disengaged from catheter hub 720 to release housing 714 from catheter hub 720.

Needle 718 includes a crimp 718b and a bushing 750 positioned proximally of crimp 718b. As discussed above with respect to previous embodiments, crimp 718b and bushing 750 prevent withdrawal of needle 718 through proximal opening 726 of housing 714 to safely retain needle tip 718a within housing 714 of safety device 713. In this embodiment, as well as in previous embodiments, the bushing 750 is not necessary and the crimp 718b can be sized to prevent retraction of the needle through a proximal opening of the safety device housing 714.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A vascular access assembly and safety device comprising:
    a catheter assembly including a catheter hub and a catheter tube extending distally from the catheter hub;
    a needle assembly including a needle having a needle tip;
    a safety device including a housing and a safety clip, the housing defining a cavity and proximal and distal openings through proximal and distal endwalls of the housing, the safety clip being formed of a resilient material and being supported within the cavity of the housing, the safety clip defining a distal opening, a central opening and a proximal opening, the distal, proximal and central openings of the safety clip being aligned with each other and with the proximal and distal openings of the housing in a first deformed position of the safety clip to slidably receive the needle, the needle retaining the safety clip in the first deformed position, wherein the housing defines a ramp positioned between the proximal and distal endwalls of the housing, the safety clip having a distal end abutting the ramp and a proximal end abutting the proximal endwall of the housing when the safety clip is in the first deformed position;
    wherein when the needle is withdrawn from the catheter assembly such that the needle tip passes through the distal opening of the safety clip, the safety clip is configured to ride up the ramp and move to a second position to obstruct distal movement of the needle tip into the distal opening of the housing.

2. The vascular access assembly and safety device of claim 1, wherein a distal end of the safety clip includes a hook portion which is positioned to engage the catheter hub when the safety clip is in the first deformed position to releasably secure the safety device to the catheter hub, the hook portion being movable to a position disengaged from the catheter hub when the safety clip moves to the second position.

3. The vascular access assembly and safety device of claim 1, wherein the safety clip is configured to move to a third position when the needle tip is withdrawn through the central opening of the safety clip to further obstruct distal movement of the needle tip through the distal opening.

4. The vascular access assembly and safety device of claim 3, wherein in the third position, the orientation of the proximal opening of the safety clip is such that the clip binds with the needle adjacent the proximal opening to obstruct proximal movement of the needle in relation to the safety clip.

5. A vascular access assembly and safety device comprising:
  a catheter assembly including a catheter hub and a catheter tube extending distally from the catheter hub;
  a needle assembly including a needle having a needle tip;
  a safety device including a housing and a safety clip, the housing defining a cavity and proximal and distal openings through proximal and distal end walls of the housing, the safety clip being formed of a resilient material and being supported within the cavity of the housing, the safety clip defining a distal opening, a central opening and a proximal opening, the distal, proximal and central openings being aligned with each other and with the proximal and distal openings of the housing in a first deformed position of the safety clip to slidably receive the needle, the needle retaining the safety clip in the first deformed position;
  wherein when the needle is withdrawn from the catheter assembly such that the needle tip passes through the distal opening of the safety clip, the safety clip is configured move to a second position to obstruct distal movement of the needle tip into the distal opening of the housing, and wherein when the needle is withdrawn from the catheter assembly such that the needle tip passes through the central opening, the safety clip is configured to move to a third position in which an orientation of the proximal opening in relation to the needle is changed to prevent further retraction of the needle.

6. The vascular access assembly and safety device of claim 5, wherein the housing defines a ramp positioned between the proximal and distal end walls of the housing, the safety clip having a distal end abutting the ramp and a proximal end abutting the proximal end wall of the housing, the safety clip being configured to ride up the ramp as the safety clip moves to the second position.

7. The vascular access assembly and safety device of claim 5, wherein a distal end of the safety clip includes a hook portion which is positioned to engage the catheter hub when the safety clip is in the first deformed position to releasably secure the safety device to the catheter hub, the hook portion being movable to a position disengaged from the catheter hub when the safety clip moves to the second position.

8. The vascular access assembly and safety device of claim 5, wherein in the third position, the orientation of the proximal opening is such that the clip binds with the needle adjacent the third opening to obstruct movement of the needle in relation to the safety clip.

* * * * *